US00PP37836P2

(12) United States Plant Patent
Growns

(10) Patent No.: US PP37,836 P2
(45) Date of Patent: Nov. 3, 2026

(54) ***ANIGOZANTHOS* PLANT NAMED 'KPSUNB'**

(50) Latin Name: ***Anigozanthos* hybrid**
Varietal Denomination: KPSUNB

(71) Applicant: Botanic Gardens and Parks Authority, Perth (AU)

(72) Inventor: Digby Growns, Perth (AU)

(73) Assignee: Botanic Gardens and Parks Authority (AU)

( * ) Notice: Subject to any disclaimer, the term of this patent is extended or adjusted under 35 U.S.C. 154(b) by 0 days.

(21) Appl. No.: 19/429,299

(22) Filed: Dec. 22, 2025

(51) Int. Cl.
*A01H 6/00* (2018.01)
*A01H 5/02* (2018.01)

(52) U.S. Cl.
USPC ..... Plt./362

(58) Field of Classification Search
USPC ..... Plt./362
CPC ..... A01H 6/00; A01H 5/02
See application file for complete search history.

*Primary Examiner* — Keith O. Robinson

(57) ABSTRACT

A new and distinct cultivar of *Anigozanthos* plant named 'KPSUNB' is disclosed, characterized by pure yellow flowers on upright plants which are drought tolerant and flower prolifically all year round. The new variety is an *Anigozanthos*, typically produced as a garden or container plant.

2 Drawing Sheets

Latin name of the genus and species: *Anigozanthos* hybrid.
Variety denomination: 'KPSUNB'.

BACKGROUND OF THE INVENTION

The new cultivar is a product of a planned breeding program. The new variety originated as the result of the crossing made during 2017 of the female parent, an unpatented, proprietary *Anigozanthos* referred to as '13/183B', and the pollen parent, *Anigozanthos* 'Bush Gold', unpatented. 'KPSUNB' was discovered and selected by the inventor at a research greenhouse in New South Wales, Australia May of 2019.

Asexual reproduction of the new cultivar 'KPSUNB' was first performed in New South Wales, Australia at a research laboratory by tissue culture during 2019. 'KPSUNB' has since produced several generations and has shown that the unique features of this cultivar are stable and reproduced true to type.

SUMMARY OF THE INVENTION

The cultivar 'KPSUNB' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KPSUNB'. These characteristics in combination distinguish 'KPSUNB' as a new and distinct *Anigozanthos* cultivar:

1. Pure yellow flower.
2. Drought tolerant.
3. Prolific flower all year round.
4. Upright plant habit.

PARENTAL COMPARISON

Plants of the new cultivar 'KPSUNB' are comparable to the seed parent in most horticultural characteristics; however, the new variety 'KPSUNB' differs in the following:

1. The new variety produces inflorescences with secondary ramification; the seed parent produces inflorescences without ramification.

Plants of the new cultivar 'KPSUNB' are comparable to the pollen parent in most horticultural characteristics; however, the new variety 'KPSUNB' differs in the following:

1. The new variety produces inflorescences with secondary ramification; the pollen parent produces inflorescences with primary ramification.

COMMERCIAL COMPARISON

Plants of the new cultivar 'KPSUNB' are comparable to the commercial *Anigozanthos* variety 'Bush Bonanza', unpatented. The two *Anigozanthos* varieties are similar in most horticultural characteristics; however, the new variety 'KPSUNB' differs in the following:

1. Ovary hair color of the new variety is yellow; the ovary hair color of this comparator is red.
2. Perianth tube profile of the new variety is parallel; perianth tube profile of this comparator is broad.
3. Perianth lobe length of the new variety is very short; perianth lobe length of this comparator is medium to long.
4. Position of the stigma in relation to the anthers of the new variety is the same level; in this comparator it is below.

BRIEF DESCRIPTION OF THE PHOTOGRAPHS

Figure 1:
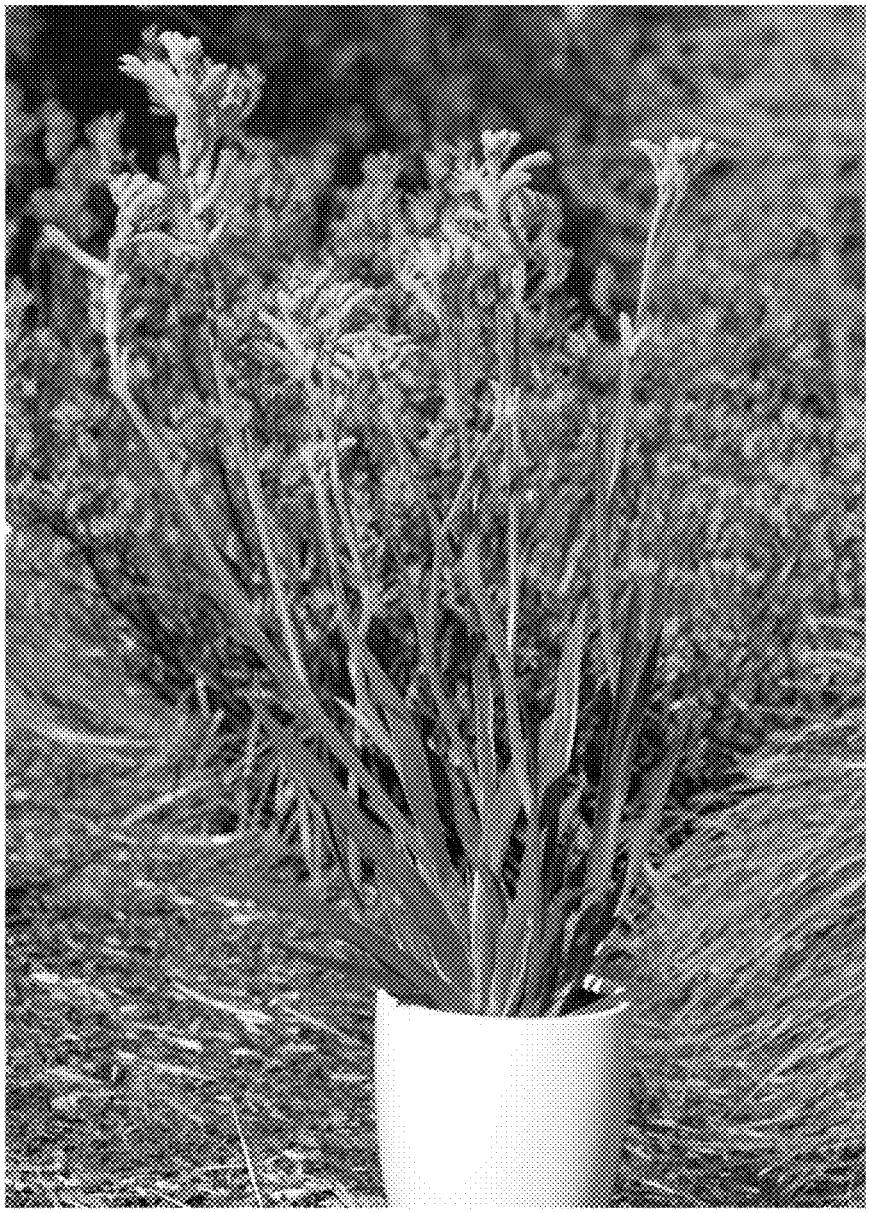

The accompanying photograph in FIG. 1 illustrates in full color a typical plant of 'KPSUNB' grown outdoors in Kangy Angy, NSW, Australia. This plant is approximately 25 weeks old, shown in a 14 cm pot.

Figure 2:
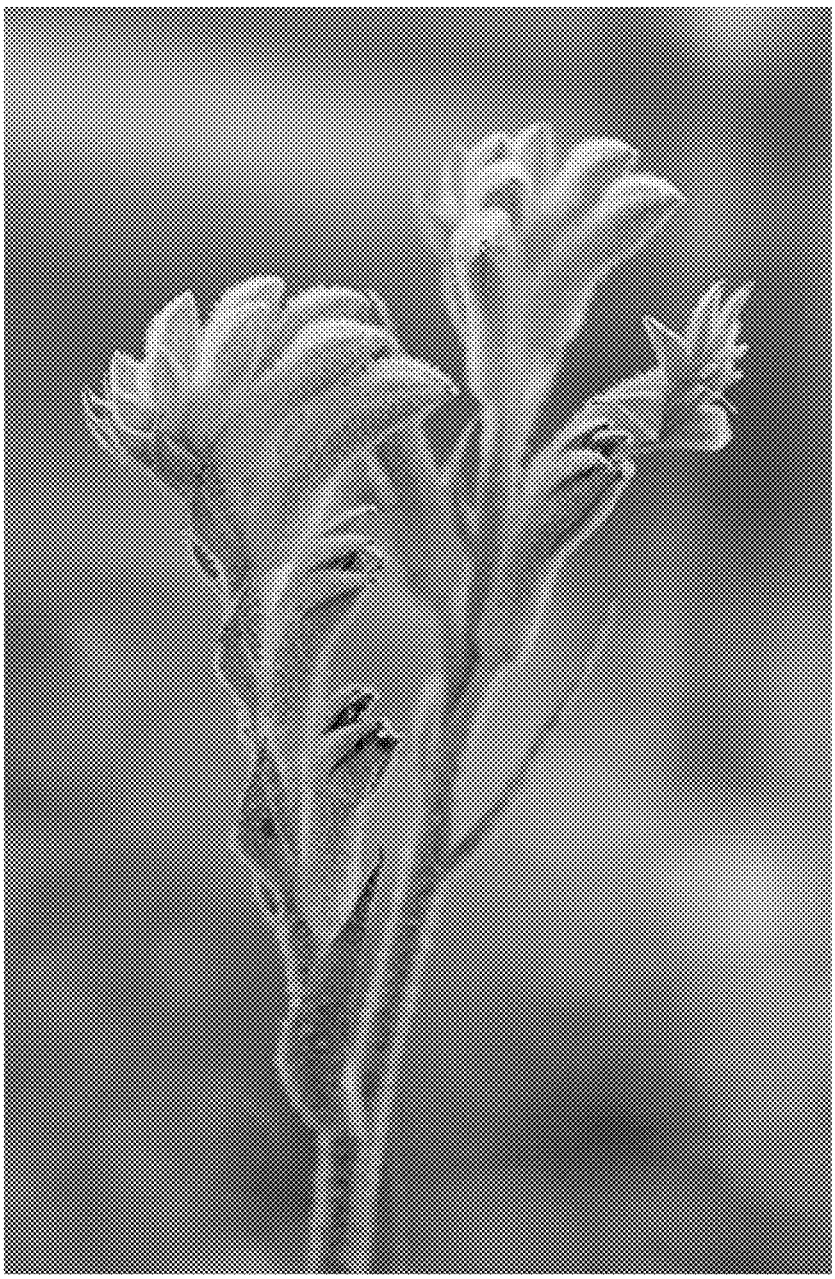

FIG. 2 illustrates a close-up view of the inflorescence.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Colour Chart, 2015, except where general terms of ordinary dictionary significance are used. The following observations and measurements describe 'KPSUNB' plants grown outdoors in full sun in Kangy Angy, NSW, Australia. Temperatures ranged from 20° C. to 32° C. during the day and 5° C. to 15° C. at night. No artificial light, photoperiodic treatments or chemical treatments were given to the plants. Measurements and numerical values represent averages of typical plant types.

Botanical classification: *Anigozanthos* hybrid 'KPSUNB'.

PROPAGATION

Time to initiate roots: 10 to 21 days at approximately 22° C. to 24° C.

Time to produce a rooted liner: 28 to 36 days at approximately 24° C. to 26° C.

PLANT

Age of plant described: Approximately 25 weeks from a rooted plantlet.

Growth habit: Compact upright fan shaped perennial with basal only branching.

Pot size: 14 cm.

Plant type: Compact upright flowering perennial.

Plant habit: Upright growing stems emerge basally.

Plant spread: Approximately 30 cm.

Height: Top of foliar plane: 30 cm.

*Top of flowering plane.*—80 cm.

Description of roots (general thickness, color, vigor, production characteristics): Thick fleshy, main roots with fine hairs and a fibrous network of smaller roots. Colored near Yellow 10D.

FOLIAGE

Leaf:

*Arrangement.*—Basally emerging, irregular rosette. Primarily fan-shaped.

Average length.—40 cm.

*Average width.*—Approximately 1.5 cm.

*Shape of blade.*—Subulate.

*Apex.*—Acuminate.

*Base.*—Clasping.

*Attachment.*—Sessile.

*Margin.*—Entire.

*Leaf attitude.*—Semi-erect and erect.

*Texture of top surface.*—Glabrous.

*Texture of lower surface.*—Glabrous.

*Appearance of top surface.*—Smooth, leathery with slight shine.

*Appearance of bottom surface.*—Smooth, leathery with slight shine.

*Color.*—Young foliage upper side: RHS 145A Strong Yellowish Green with 54B Deep Purplish Pink anthocyanin coloration at basal section of leaf. Young foliage under side: RHS 145A Strong Yellowish Green with 54B Deep Purplish Pink anthocyanin coloration at basal section of leaf. Mature foliage upper side: RHS 146C Moderate Yellowish Green with 54B Deep Purplish Pink anthocyanin coloration at basal section of leaf. Mature foliage under side: RHS 146C Moderate Yellowish Green with 54B Deep Purplish Pink anthocyanin coloration at basal section of leaf.

*Venation.*—Type: Parallel. Venation color upper side: RHS Yellow-Green 146D. Venation color under side: RHS Yellow-Green 146D.

*Petiole.*—Not Present.

FLOWER

Natural flowering season: Freely flowering under outdoors growing conditions with substantially continuous blooming from Spring through Autumn.

Inflorescence and flower type and habit: Secondary ramification present. Large flowers arranged singly on terminal racemes. Individual flowers are zygomorphic, tubular, with a curved perianth.

Inflorescence height: Approximately 9 to 10 cm.

Inflorescence width: Approximately 6.5 cm.

Flower longevity on plant: Individual flowers last approximately 30 days.

Approximate quantity of flowers per plant: 10 to 16 inflorescences per plant. Each inflorescence has about 15 flowers and buds per inflorescence.

Persistent or self-cleaning: Persistent.

Bud:

*Shape.*—Tubular.

*Length.*—About 2 cm.

*Diameter.*—About 5 mm.

*Texture.*—Pilous.

*Color.*—Yellow 13C, brilliant yellow.

Flower size:

*Diameter.*—Approximately 3.5 cm (apical section open).

*Length.*—Approximately 7.5 cm.

Petals (unfused floral section):

*Length.*—Approximately 1.2 cm.

*Diameter.*—Approximately 0.2 cm.

*Quantity.*—6 to 8.

*Texture.*—Exterior covered in dense, pilous hairs. Interior glabrous.

*Apex.*—Acute.

*Color.*—When opening: Outer, visible surface: 14B Vivid Yellow. Fully opened: Outer surface: 14B Vivid Yellow. Inner surface: RHS Yellow-Green 150B, Brilliant yellow green.

Perianth tube:

*Length.*—Approximately 4 cm.

*Diameter.*—Approximately 0.7 cm.

*Texture.*—Outer texture highly pubescent, inner texture glabrous.

*Description.*—Flared distally.

*Color.*—When opening: Outer, visible surface, including perianth hair color: 149B Brilliant Yellow Green flesh with 14B Vivid Yellow dense hairs. Fully opened: Outer surface, including perianth hair color: 149B Brilliant Yellow Green flesh with 14B Vivid Yellow dense hairs. Inner surface: RHS 150B Brilliant Yellow Green.

*Floral bracts*.—Quantity: 14. Shape: Narrow deltoid. Tip: Acuminate. Base: Clasping. Texture: Pilous on lower surface, glabrous on upper surface. Length: Approximately 3.0 cm. Width: Approximately 0.4 cm. Color: Upper surface: RHS 150B Brilliant Yellow Green. Lower surface: RHS 143A Strong Yellow Green flesh with 14B Vivid Yellow dense hairs.

Peduncle:

*Length*.—40 to 80 cm.

*Diameter*.—0.4 cm.

*Color*.—RHS 143A Strong Yellow Green scape with 14B Vivid Yellow dense hairs.

*Aspect*.—Straight.

*Strength*.—Very strong.

*Texture*.—Pilous.

Pedicels:

*Length*.—Average range 0.8 cm to 1 cm.

*Diameter*.—0.2 cm.

*Color*.—RHS 143A Strong Yellow Green with 14B Vivid Yellow dense hairs.

*Orientation*.—Approximately 45 degrees from peduncle.

*Strength*.—Strong.

*Texture*.—Pilous.

Sepals not Present.

Nectaries not observed.

Fragrance: None.

REPRODUCTIVE ORGANS

Androecium:

Stamens:

*Number*.—6.

Anthers:

*Quantity at top of perianth*.—6.

*Shape*.—Ovoid.

*Length*.—Approximately 0.5 cm.

*Color*.—RHS Yellow-Green 144A.

*Pollen*.—Color: RHS Yellow 11A. Quantity: Moderate.

Gynoecium:

Pistil:

*Number*.—1.

*Length*.—0.8 cm.

*Style*.—Length: 0.4 cm. Color: RHS Yellow-Green 144A.

*Stigma*.—Shape: Rounded. Color: RHS Yellow-Green N144B. Ovary Color: RHS Yellow-Green 144A.

OTHER CHARACTERISTICS

Seeds and fruits: Not observed to date.

Disease/pest resistance: Neither resistance nor susceptibility to the normal diseases and pests of *Anigozanthos* has been observed.

Temperature tolerance: From approximately 0° C. to more than 40° C.

Drought tolerance: Observed.

What is claimed is:

1. A new and distinct cultivar of *Anigozanthos* plant named 'KPSUNB' as herein illustrated and described.

* * * * *